United States Patent [19]

Barner et al.

[11] Patent Number: 4,675,421
[45] Date of Patent: Jun. 23, 1987

[54] HYDROQUINONE DERIVATIVES AND A PROCESS FOR THEIR PREPARATION

[75] Inventors: Richard Barner, Witterswil; Josef Hübscher, Seon, both of Switzerland

[73] Assignee: Hoffmann-La Roche Inc., Nutley, N.J.

[21] Appl. No.: 768,789

[22] Filed: Aug. 23, 1985

[30] Foreign Application Priority Data

Aug. 28, 1984 [CH] Switzerland ............... 4117/84
Jul. 11, 1985 [CH] Switzerland ............... 3000/85

[51] Int. Cl.[4] ............................................. C07B 49/00
[52] U.S. Cl. ........................................ 549/416; 556/9; 556/54; 560/53; 568/811; 568/649; 562/463; 260/397.5
[58] Field of Search .................. 556/54, 9; 549/416; 568/649, 765

[56] References Cited

U.S. PATENT DOCUMENTS

| | | | |
|---|---|---|---|
| 4,151,205 | 4/1979 | Cohen et al. | 549/416 |
| 4,153,614 | 5/1979 | Barner et al. | 568/649 |
| 4,163,021 | 7/1979 | Cohen et al. | 549/416 |
| 4,277,610 | 7/1981 | Cohen et al. | 549/416 |
| 4,598,160 | 7/1986 | Truesdale | 549/416 |

OTHER PUBLICATIONS

Whitesell et al., Asymmetric Induction, Ene Reactions of a Chiral Glyoxylate Ester, J. Chem. Soc. Commun., 1982, pp. 989-999.
Whitesell et al., Asymmetric Induction, Reduction, Nucleophilic Addition to, and Ene Reactions of Chiral-Ketoesters.
Seeback et al., Titanium and Zirconium Derivatives in Organic Synthesis, Modern Snyth. Methods, 1983, p. 217 ff.

Primary Examiner—Glennon H. Hollrah
Assistant Examiner—A. A. Owens
Attorney, Agent, or Firm—Jon S. Saxe; George M. Gould; Julie M. Prlina

[57] ABSTRACT

Compound of the general formula

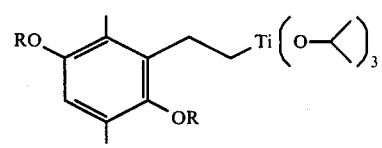

wherein R represents an ether protecting group useful as intermediates.

3 Claims, No Drawings

HYDROQUINONE DERIVATIVES AND A PROCESS FOR THEIR PREPARATION

The present invention is concerned with a novel process for the manufacture of novel hydroquinone derivatives which are useful as intermediates for the manufacture of d-α-tocopherol (natural vitamin E). The invention is also concerned with novel starting materials in this process.

Several processes for the manufacture of natural vitamin E are known, but these are only of limited interest from the industrial point of view. Accordingly, natural vitamin E has hitherto been extracted almost exclusively from natural sources. There accordingly exists a need for an industrially realizable approach according to which natural vitamin E can be obtained in good yield and with high optical purity.

The process in accordance with the invention comprises
(a) reacting a compound of the general formula

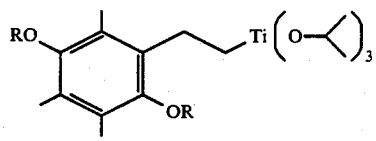

wherein R represents an ether protecting group, with a ketoester of the formula

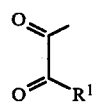

wherein $R^1$ represents a residue of the formula

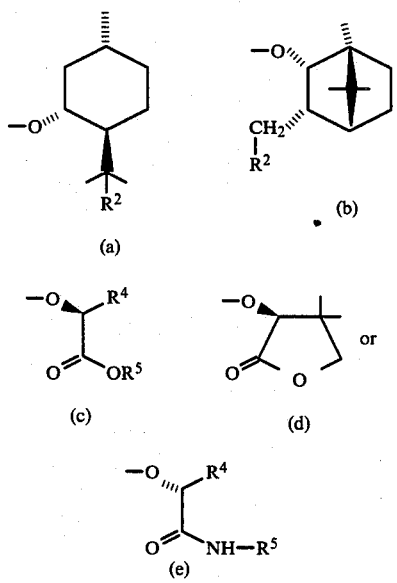

in which $R^2$ signifies phenyl, $R^4$ signifies methyl or phenyl and $R^5$ signifies lower alkyl, aryl or aryl-lower alkyl,
and, if desired, hydrolyzing a thus-obtained compound of the general formula

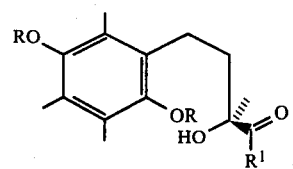

wherein R and $R^1$ have the above significance, to a compound of the general formula

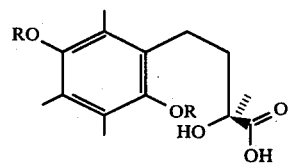

wherein R has the above significance,
or reducing a compound of general formula III to a compound of the general formula

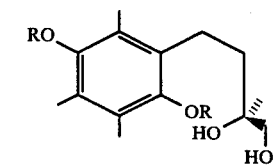

wherein R has the above significance, or
(b) reacting the compound of the formula

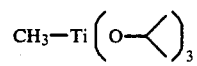

with a compound of the general formula

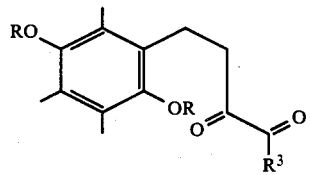

wherein R has the above significance and $R^3$ represents a residue of the formula

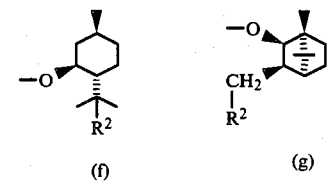

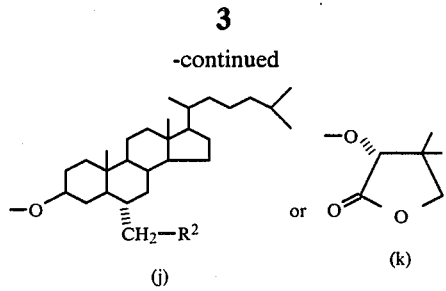

in which $R^2$, $R^4$ and $R^5$ have the above significance,
and, if desired, hydrolyzing a thus-obtained compound of the general formula

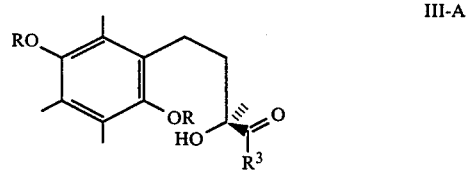

III-A wherein R and $R^3$ have the above significance,
to a compound of general formula IV or reducing a compound of general formula III-A to a compound of general formula V.

The term "ether protecting group" signifies in the scope of the present invention not only groups which are cleavable by hydrolysis such as, for example, the silyl group or alkoxymethyl groups, for example the methoxymethyl group, or also the tetrahydropyranyl group, but also groups which are cleavable oxidatively such as, for example, $C_1-C_6$-alkyl ether groups.

The term "lower alkyl" signifies in the scope of the present invention straight-chain or branched alkyl groups with 1–6 carbon atoms such as methyl, ethyl, propyl, isopropyl, n-butyl, isobutyl, tert.butyl, pentyl, hexyl and the like. The term "aryl" signifies not only phenyl but also naphthyl which can be not only substituted but also unsubstituted. In the term "aryl-lower alkyl" aryl and lower alkyl have the previous significance.

Furthermore, in the formulae herein a solid tapering line "∇" indicates that the corresponding residue is situated above the plane of the molecule, while a series of parallel lines "≡" indicates that the corresponding residue is situated below the plane of the molecule.

The compounds of formulae I, III, III-A, IV and VII are novel and are likewise objects of the present invention.

The reaction of a compound of formula I with a ketoester of formula II is conveniently carried out in an inert organic solvent at a temperature of about −80° C. to about +10° C., preferably at about −20° C. to about 0° C. As solvents there can be mentioned here especially those which are usually used in metal-organic reactions, especially ethers such as, for example, diethyl ether, tert.butyl methyl ether, tetrahydrofuran and the like.

The hydrolysis of a compound of formula III to a hydroxyacid of general formula IV can be carried out in a manner known per se. This hydrolysis is conveniently carried out in a suitable organic solvent such as, for example, a lower alcohol with 1–5 carbon atoms, e.g. methanol, ethanol and the like, using an alkali metal hydroxide or alkaline earth metal hydroxide, preferably sodium hydroxide or potassium hydroxide.

The reduction of a compound of formula III to a compound of formula V can be carried out in a manner known per se. This reduction is conveniently carried out using complex metal hydrides such as e.g. $LiAlH_4$, $LiBH_4$, diisobutylaluminium hydride and the like. As solvents there come into consideration inert organic solvents, especially ethers such as diethyl ether or tetrahydrofuran and the like. The temperature and pressure at which this reduction is carried out are not critical, and accordingly the reduction can be carried out under the conditions which are usual for the reduction of esters to alcohols.

The ketoesters of formula II which are used as starting materials are known compounds or analogues of known compounds which can be prepared readily in a manner analogous to the preparation of the known compounds. The compounds of formula I which are also used as starting materials are, however, novel and can be prepared in accordance with the following Reaction Scheme:

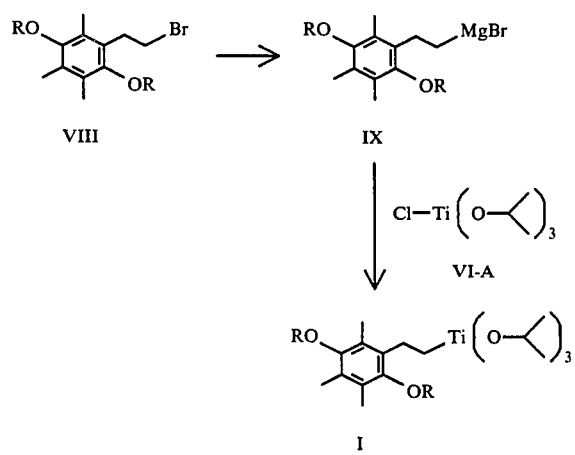

wherein R has the above significance.

The conversion of the compounds of formula VIII into the Grignard compounds of formula IX can be carried out under the conditions which are usual for the preparation of Grignard compounds.

The reaction of a Grignard compound of formula IX with the compound of formula VI-A can be carried out in a manner known per se. This reaction is conveniently carried out at about −80° C. to about 0° C., preferably at −20° C. As solvents there can be used all solvents which also come into consideration in the preparation of Grignard compounds.

The reaction of the compound of formula VI with a compound of formula VII can be carried out in a manner known per se, especially in a manner analogous to the reaction of a compound of formula I with a ketoester of formula II.

The compound of formula VI which is used as the starting material is known. The compounds of formula VII which are also used as starting materials are, however, novel and are likewise an object of the present invention. They can be prepared as illustrated in the following Scheme.

Scheme

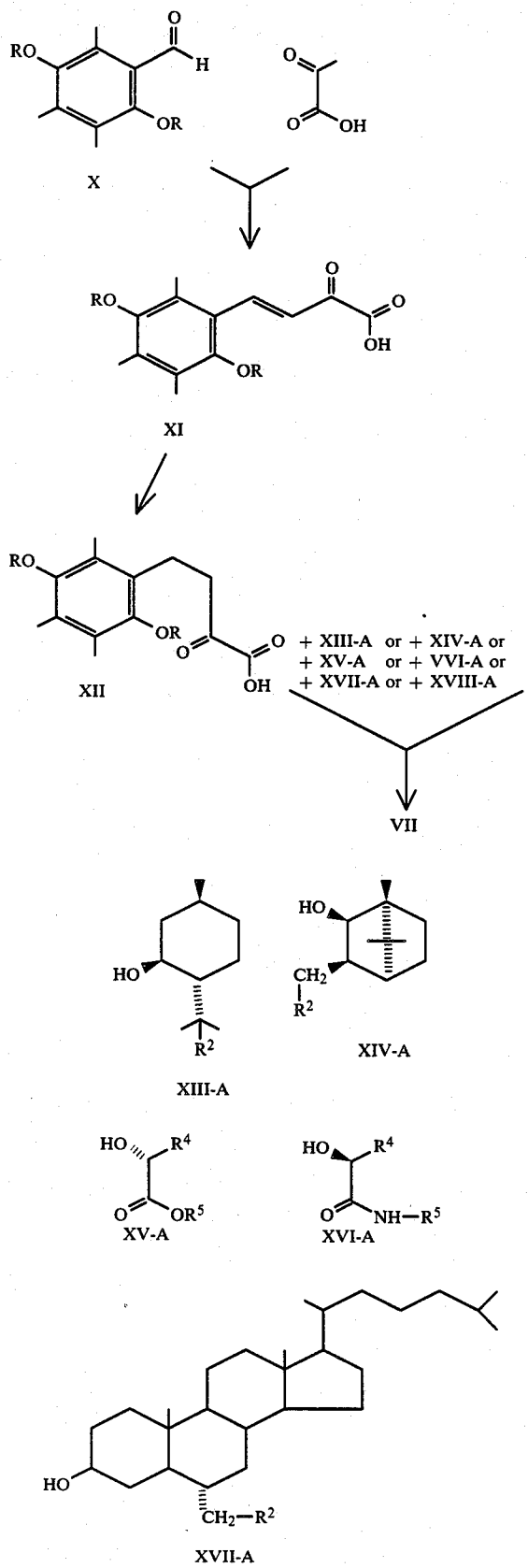

-continued
Scheme

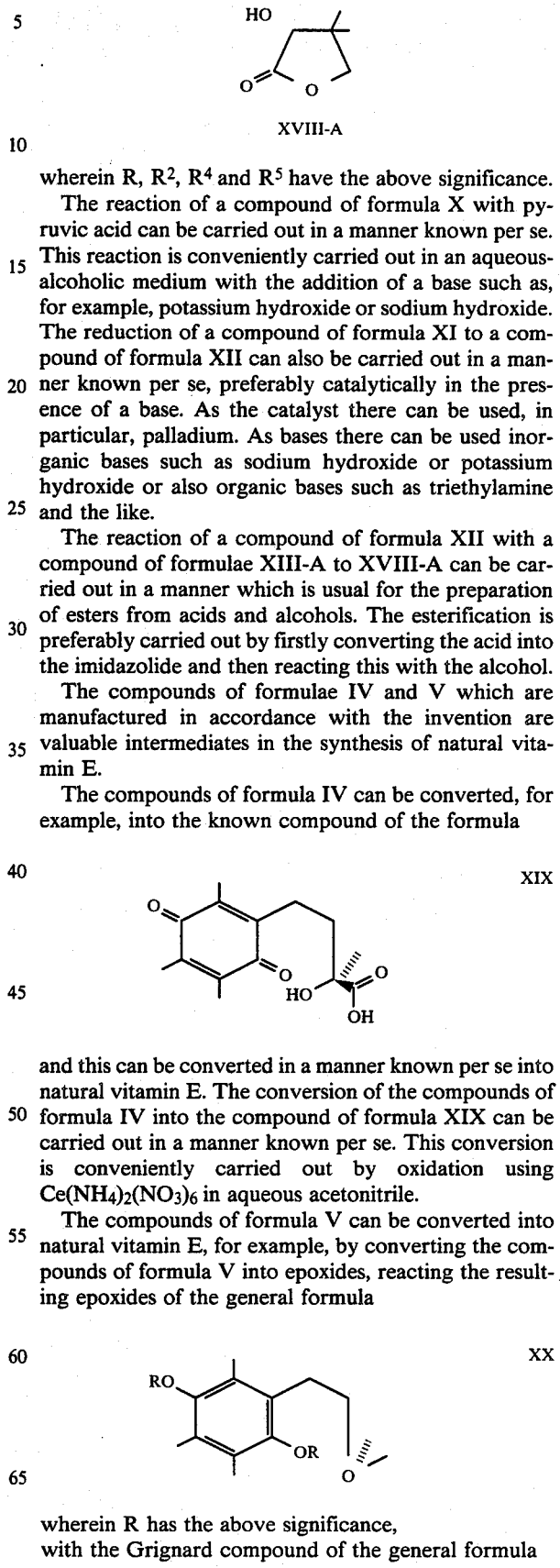

wherein R, $R^2$, $R^4$ and $R^5$ have the above significance.

The reaction of a compound of formula X with pyruvic acid can be carried out in a manner known per se. This reaction is conveniently carried out in an aqueous-alcoholic medium with the addition of a base such as, for example, potassium hydroxide or sodium hydroxide. The reduction of a compound of formula XI to a compound of formula XII can also be carried out in a manner known per se, preferably catalytically in the presence of a base. As the catalyst there can be used, in particular, palladium. As bases there can be used inorganic bases such as sodium hydroxide or potassium hydroxide or also organic bases such as triethylamine and the like.

The reaction of a compound of formula XII with a compound of formulae XIII-A to XVIII-A can be carried out in a manner which is usual for the preparation of esters from acids and alcohols. The esterification is preferably carried out by firstly converting the acid into the imidazolide and then reacting this with the alcohol.

The compounds of formulae IV and V which are manufactured in accordance with the invention are valuable intermediates in the synthesis of natural vitamin E.

The compounds of formula IV can be converted, for example, into the known compound of the formula and this can be converted in a manner known per se into natural vitamin E. The conversion of the compounds of formula IV into the compound of formula XIX can be carried out in a manner known per se. This conversion is conveniently carried out by oxidation using $Ce(NH_4)_2(NO_3)_6$ in aqueous acetonitrile.

The compounds of formula V can be converted into natural vitamin E, for example, by converting the compounds of formula V into epoxides, reacting the resulting epoxides of the general formula wherein R has the above significance,
with the Grignard compound of the general formula

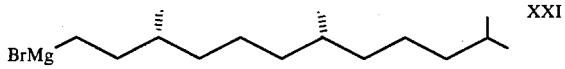

and converting the thus-obtained known compounds of the general formula

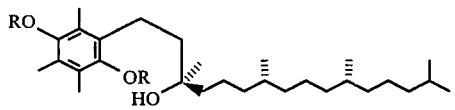

wherein R has the above significance, into d-α-tocopherol in a known manner.

The conversion of a compound of formula V into an epoxide of formula XX can be carried out in a manner known per se. For this purpose, the primary hydroxy group in a compound of formula V is firstly converted into a leaving group, e.g. into a halide (chlorine, bromine and iodine coming into consideration as the halogen) or into a sulphonic acid ester (e.g. tosylate or mesylate) and the like. This can be carried out in a manner known per se. The thus-obtained compound is subsequently treated with a base. As bases there are suitable not only inorganic bases but also organic bases, preferably inorganic bases such as especially sodium hydroxide or potassium hydroxide and the like.

The reaction of an epoxide of formula XX with the Grignard compound of formula XXI can be carried out in a manner known per se. However, it is preferred to carry out the reaction in the presence of copper (I or II) catalysts, especially copper(I)-n-propylacetylide or a copper(I) halide-dimethyl sulphide complex. As solvents for this reaction there are suitable all solvents which usually come into consideration in Grignard reactions.

The compounds of general formula XXII are known and can be converted into d-α-tocopherol in a known manner.

EXAMPLE 1

A solution of 18.6 mmol of 2-(2',5'-dimethoxy-3',4',6'-trimethylphenyl)-ethyl triisopropoxytitanium in 20 ml of tetrahydrofuran is treated dropwise at −20° C. while stirring with 3.12 g (10.3 mmol) of (−)-8-phenylmenthyl pyruvate and the mixture is subsequently left to stand at −20° C. for a further 16 hours. After the addition of 50 ml of aqueous sodium dihydrogen phosphate solution (10%) the mixture is extracted three times with 50 ml of ether each time. The combined organic phases are dried over sodium sulphate and the solvent is then removed on a rotary evaporator. There are obtained 6.76 g of (−)-8-phenylmenthyl (S)-4-(2',5'-dimethoxy-3',4',6'-trimethylphenyl)-2-hydroxy-2-methylbutanoate.

The 2-(2',5'-dimethoxy-3',4',6'-trimethylphenyl)-ethyl triisopropoxytitanium which is used as the starting material can be prepared as follows:

5.34 g (18.6 mmol) of 1-(2-bromoethyl)-2,5-dimethoxy-3,4,6-trimethylbenzene are heated at reflux for 1 hour in 20 ml of dry tetrahydrofuran with 0.50 g (20.8 mmol) of magnesium. 4.71 ml (19.0 mmol) of chlorotriisopropoxy-titanium are then added at −20° C. The solution of the resulting 2-(2',5'-dimethoxy-3',4',6'-trimethylphenyl)-ethyl triisopropoxytitanium is processed directly.

EXAMPLE 2

A solution of 0.907 g (about 1.35 mmol) of (−)-8-phenylmenthyl (S)-4-(2',5'-dimethoxy-3',4',6'-trimethylphenyl)-2-hydroxy-2-methylbutanoate in 10 ml of ethanol is treated with 1 ml of 28% sodium hydroxide solution and the mixture is left to stand at room temperature for 16 hours. The mixture is then diluted with 50 ml of water and extracted three times with 50 ml of ether each time. The aqueous phase is acidified (pH 2) with 10% phosphoric acid and extracted three times with 50 ml of ether each time. The combined organic phases are dried over sodium sulphate and the solvent is subsequently removed on a rotary evaporator. There are obtained 212 mg of (S)-4-(2',5'-dimethoxy-3',4',6'-trimethylphenyl)-2-hydroxy-2-methylbutanoic acid.

EXAMPLE 3

A solution of 6.76 g (about 10.3 mmol) of (−)-8-phenylmenthyl (S)-4-(2',5'-dimethoxy-3',4',6'-trimethylphenyl)-2-hydroxy-2-methylbutanoate in 50 ml of dry ether is added dropwise while stirring to a suspension of 0.380 g (9.98 mmol) of LiAlH$_4$ in 10 ml of ether. After stirring at room temperature for a further 2 hours 10 ml of ethyl acetate are added dropwise (decomposition of excess LiAlH$_4$) and subsequently 10 ml of 10% aqueous sodium dihydrogen phosphate solution are added dropwise. The reaction mixture is extracted three times with 50 ml of ether each time, the combined organic phases are dried over sodium sulphate and the solvent is removed on a rotary evaporator, whereby 4.61 g of crude (S)-4-(2',5'-dimethoxy-3',4',6'-trimethylphenyl)-2-methyl-1,2-butanediol are obtained. The crude product is reprecipitated from 10 ml of ether and 40 ml of hexane and gives 1.68 g of the pure diol as a white product.

M.p. 85°–86° C.; $[\alpha]_D^{25} = +2.79°$ (c=2% in chloroform).

In the $^1$H-NMR (60 MHz) using Eu(HFC)$_3$ as the chiral shift reagent the compound, as the acetonide, is found to be optically pure (e.e. >90%).

EXAMPLE 4

A solution of 0.78 mmol of 2-(2',5'-dimethoxy-3',4',6'-trimethylphenyl)-ethyl triisopropoxytitanium (prepared according to Example 1) in 10 ml of dry tetrahydrofuran is treated while stirring at −20° C. with 0.30 g (0.95 mmol) of (+)-cis-3-benzylbornyl pyruvate and the mixture is subsequently left to stand at −20° C. for a further 16 hours. The working-up is carried out in a manner analogous to that described in Example 1 and there is obtained (+)-cis-3-benzylbornyl (S)-4-(2',5'-dimethoxy-3',4',6'-trimethylphenyl)-2-hydroxy-2-methylbutanoate which is saponified directly in a manner analogous to that described in Example 2. The aqueous phase which is thereby obtained is treated with 0.5 ml of dimethyl sulphate and 20 mg of Aliquat 336 (a phase transfer catalyst from the firm Fluka/CH) and the mixture is stirred at room temperature for 1 hour. 1 ml of 25% ammonia is added and the resulting mixture is stirred at room temperature for a further 1 hour (removal of excess dimethyl sulphate). By extracting the reaction mixture with ether, drying the ether phase over sodium sulphate and removing the solvent there are obtained 150 mg of methyl (S)-4-(2',5'-dimethoxy-3',4',6'-trimethylphenyl)-2-hydroxy-2-methylbutanoate. Optical purity according to HPLC on a "Pirkle Phase"=95% e.e.

The (+)-cis-3-benzylbornyl pyruvate which is used as the starting material can be prepared as follows:

A solution of 0.88 g (10 mmol) of pyruvic acid in 20 ml of dry methylene chloride is treated with 2.2 g (10 mmol) of carbonyldiimidazole and the mixture is stirred until the evolution of gas has finished (about 10 minutes). To the thus-obtained solution of pyruvic acid imidazolide there are added 3.7 g (10 mmol) of (+)-cis-3-benzylborneol in dry methylene chloride together with 1 mmol of imidazole lithium as the catalyst. The mixture is stirred overnight at room temperature, subsequently taken up with water and ether, the ether phase is filtered through silica gel, the filtrate is concentrated and the residue is distilled in a high vacuum ($10^{-2}$ Torr) at about 190° C. There are obtained 4.5 g of (+)-cis-3-benzylbornyl pyruvate. Thin-layer chromatography: (silica gel:toluene/ethyl acetate 10:1): Rf=0.4.

EXAMPLE 5

A solution of 1.4 g (2.68 mmol) of (−)-cis-3-benzylbornyl 4-(2′,5′-dimethoxy-3′,4′,6′-trimethylphenyl)-2-ketobutanoate in 20 ml of dry tetrahydrofuran is treated while stirring at −20° C. with 3 mmol of methyl-triisopropoxytitanium in 1 ml of hexane and this mixture is subsequently left to stand at −20° C. for a further 16 hours. The working-up is carried out in a manner analogous to that described in Example 1 and there is obtained (−)-cis-3-benzylbornyl (S)-4-(2′,5′-dimethoxy-3′,4′,6′-trimethylphenyl)-2-hydroxy-2-methylbutanoate which is converted into the methyl ester in a manner analogous to that described in Example 4.

Optical purity according to HPLC on a "Pirkle Phase": 70% e.e. The optical purity of the (−)-borneol originally used was also 70% e.e.

The experiment carried out with optically pure (+)-borneol in a manner analogous to the foregoing gave the corresponding (R)-methyl ester with an optical purity of 95% e.e.

The (−)-cis-3-benzylbornyl 4-(2′,5′-dimethoxy-3′,4′,6′-trimethylphenyl)-2-ketobutanoate which is used as the starting material can be prepared starting from 4-(2′,5′-dimethoxy-3′,4′,6′-trimethylphenyl)-2-ketobutanoic acid and (−)-cis-3-benzylborneol in a manner analogous to that described in Example 4.

The aforementioned 4-(2′,5′-dimethoxy-3′,4′,6′-trimethylphenyl)-2-ketobutanoic acid can be prepared as follows:

A suspension of 3.7 g (17.6 mmol) of 2,5-dimethoxy-3,4,6-trimethylbenzaldehyde and 5.0 g (53.2 mmol) of sodium pyruvate in 20 ml of methanol is treated with 0.1 g (1.8 mmol) of potassium hydroxide and the mixture is subsequently heated at reflux for 5 hours, whereby a yellow solution is obtained. The reaction mixture is poured on to ice-water and the resulting 4-(2′,5′-dimethoxy-3′,4′,6′-trimethylphenyl)-2-keto-3-butenoic acid is precipitated by the addition of sulphuric acid while stirring. The suspension is stirred for 1 hour, filtered, the filter residue is washed with water and dried. In this manner there are obtained 4.9 g of 4-(2′,5′-dimethoxy-3′,4′,6′-trimethylphenyl)-2-keto-3-butenoic acid in the form of a yellow powder of melting point 126°–127° C.

1.02 g (3.5 mmol) of this powder in 80 ml of water are hydrogenated over 400 mg of Pd/C (5%) under normal pressure with the addition of 10 ml of 1N sodium hydroxide solution until the control by thin-layer chromatography indicates complete hydrogenation. The catalyst is filtered off, the filtrate is acidified to pH 4 with phosphoric acid and extracted with ether. By evaporation of the ether extracts, dried over sodium sulphate, there is obtained 0.75 g of 4-(2′,5′-dimethoxy-3′,4′,6′-trimethylphenyl)-2-ketobutanoic acid.

EXAMPLE 6

In a manner analogous to that described in Example 5, (1S)-1-benzylcarbamyl-ethyl 4-(2′,5′-dimethoxy-3′,4′,6′-trimethylphenyl)-2-ketobutanoate is reacted with methyl-triisopropoxytitanium firstly at −78° C. for 5 hours and then at −20° C. for 16 hours and the reaction product is then converted into the methyl ester. The optical purity is above 95% e.e. according to HPLC on a "Pirkle Phase".

The (1S)-1-benzylcarbamyl-ethyl 4-(2′,5′-dimethoxy-3′,4′,6′-trimethylphenyl)-2-ketobutanoate which is used as the starting material can be prepared from 4-(2′,5′-dimethoxy-3′,4′,6′-trimethylphenyl)-2-ketobutanoic acid and (1S)-1-(benzylcarbamyl)ethanol (=L-lactic acid benzylamide) in a manner analogous to that described in Example 4.

EXAMPLE 7

148 mg (0.5 mmol) of (S)-4-(2′,5′-dimethoxy-3′,4′,6′-trimethylphenyl)-2-hydroxy-2-methylbutanoic acid (prepared according to Example 2) are dissolved in 2 ml of acetonitrile, the solution is treated while stirring with 560 mg (1 mmol) of Ce(NH$_4$)$_2$(NO$_3$)$_6$ in 2 ml of water and the mixture is subsequently stirred at room temperature for a further 10 minutes. The mixture is then treated with 50 ml of water and extracted three times with 50 ml of chloroform each time. After drying over sodium sulphate the combined organic phases are concentrated and there are thus obtained 111 mg of (+)-(S)-2-hydroxy-2-methyl-4-(2′,4′,5′-trimethyl-3′,6′-dioxo-1′,4′-cyclohexadien-1′-yl)butanoic acid.

M.p. 115°–117° C.; $[\alpha]_D^{25} = +11°$ (c=0.2% in chloroform); optical purity of the educt according to HPLC on a "Pirkle Phase" 95% e.e.

The product which is obtained after catalytic reduction and subsequent acidic cyclization, i.e. (−)-(S)-6-hydroxy-2,5,7,9-tetramethylchromane-2-carboxylic acid, is obtained optically pure after recrystallization from toluene.

$[\alpha]_D^{25} = -68.8°$ (c=1% in chloroform).

EXAMPLE 8

(a) 237 mg of tosyl chloride and 350 mg of (S)-4-(2′,5′-dimethoxy-3′,4′,6′-trimethylphenyl)-2-methyl-1,2-butanediol are dissolved in 1 ml of methylene chloride. 0.180 ml of pyridine are then added dropwise at 0° C. and the mixture is left to stand at 0° C. for 1 hour and then at room temperature for 16 hours. Thereupon, 1 g of ice and 0.3 ml of concentrated hydrochloric acid are added. The mixture is then extracted with methylene chloride, and the extract is dried and concentrated. There are obtained 511 mg (95%) of (S)-4-(2′,5′-dimethoxy-3′,4′,6′-trimethylphenyl)-2-methyl-1-toluenesulphonyloxy-2-butanol.

$[\alpha]_D^{20} = +1.2°$ (c=2.6% in chloroform).

(b) 177 mg of (S)-4-(2′,5′-dimethoxy-3′,4′,6′-trimethylphenyl)-2-methyl-1-toluenesulphonyloxy-2-butanol are dissolved in 1 ml of ethanol and the solution is treated with 0.3 ml of alcoholic sodium hydroxide solution (1.5N). The mixture is left to stand at room temperature for 10 minutes, 30 ml of methylene chloride are then added and the mixture was dried over sodium sulphate and concentrated. There are obtained 105 mg of (S)-4-(2′,5′-dimethoxy-3′,4′,6′-trimethylphenyl)-2-methyl-1,2-epoxybutane. M.p. 47°–48° C.

$[\alpha]_D^{20} = +4.91°$ (c=2.2% in chloroform).

(c) 5.8 mmol of (3R,7R)-3,7,11-trimethyldodecyl bromide are heated at reflux for ¼ hour in 20 ml of ethyl acetate with activated magnesium. Then, there are added at 0° C. 1 g of (S)-4-(2',5'-dimethoxy-3',4',6'-trimethylphenyl)-2-methyl-1,2-epoxybutane and 0.9 g of copper(I)-2-propylacetylide [or 1.2 g of copper(I) bromide/dimethyl sulphide complex]. The temperature of the reaction mixture is subsequently left to rise to room temperature and the mixture is stirred overnight. 10 ml of ammonium chloride are then added and the mixture is extracted with ethyl ether. The extract is dried and concentrated, and the residue is distilled in a bulb-tube (b.p.$_{0.01}$=140° C.). There are obtained 1.28 g (72%) [or 1.41 g (79%)] of (3R,7R,11R)-1-(2',5'-dimethoxy-3',4',6'-trimethylphenyl)-3,7,11,15-tetramethylhexadecan-3-ol as a colourless oil.

$[\alpha]_D^{20} = -0.67°$ (c=0.9% in chloroform).

$C_{31}H_{56}O_3$ (476.79): Calc: C=78.09 H=11.84. Found: C=77.92 H=11.88.

We claim:

1. Compounds of the general formula

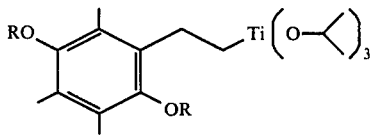

wherein R represents an ether protecting group.

2. Compounds according to claim 1 wherein the ether protecting group signifies silyl group, alkoxymethyl group, tetrahydropyranyl group or $C_1$-$C_6$ alkyl.

3. Compounds according to claim 1 where the ether protecting group is methyl.

* * * * *